United States Patent [19]

Jonas et al.

[11] Patent Number: 4,477,454

[45] Date of Patent: Oct. 16, 1984

[54] 2-ARYLTETRAAZAINDENES FOR TREATING CARDIAC INSUFFICIENCY

[75] Inventors: Rochus Jonas, Darmstadt; Michael Kloft; Hanns Wurziger, both of Darmstadt-Arheilgen; Juergen Harting; Hans J. Enenkel, both of Darmstadt; Klaus-Otto Minck, Ober-Ramstadt; Hans-Jochen Schliep, Traisa, all of Fed. Rep. of Germany

[73] Assignee: Merck Patent Gesellschaft mit Beschrankter Haftung, Darmstadt, Fed. Rep. of Germany

[21] Appl. No.: 492,909

[22] Filed: May 9, 1983

[30] Foreign Application Priority Data

May 11, 1983 [DE] Fed. Rep. of Germany ....... 3217583

[51] Int. Cl.³ ................ A61K 31/495; C07D 487/00
[52] U.S. Cl. ..................... 424/250; 544/236; 544/350
[58] Field of Search ............... 544/236, 350; 424/250

[56] References Cited

U.S. PATENT DOCUMENTS

| 3,660,397 | 5/1972 | Jones et al. | 544/350 |
| 4,072,746 | 2/1978 | Lesher et al. | 424/263 |
| 4,327,100 | 4/1982 | Austel et al. | 424/256 |
| 3,244,715 | 4/1966 | Castle | 544/236 |

OTHER PUBLICATIONS

Arzneimittelforschung, vol. 31 (I) No. 1a (1981, pp. 141 to 278.

Primary Examiner—Donald G. Daus
Assistant Examiner—Cecilia Shen
Attorney, Agent, or Firm—Millen & White

[57] ABSTRACT

2-Aryltetraazaindenes of the formula

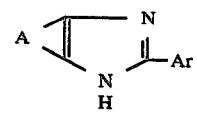

wherein —A— is —N=CH—CH=N— or —CH=N—N=CH—, Ar is unsubstituted phenyl or phenyl mono-, di- or tri-substituted by hydroxyl, mercapto, dialkylamino, trifluoromethyl and/or —Z—R groups, Z is —O—, —S— or —SO— and R is alkyl, alkenyl, alkynyl or cyanomethyl, the alkyl, alkenyl and alkynyl groups each having up to 5 C atoms, and their physiologically acceptable salts, exhibit blood pressure, myocardial contraction, and anti-ulcer activities.

7 Claims, No Drawings

2-ARYLTETRAAZAINDENES FOR TREATING CARDIAC INSUFFICIENCY

BACKGROUND OF THE INVENTION

This invention relates to 2-aryltetraazaindenes of the general formula I

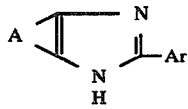

wherein —A— is —N=CH—CH=N— or —CH=N—N=CH—, Ar is unsubstituted phenyl or phenyl mono-, di- or tri-substituted by hydroxyl, mercapto, dialkylamino, trifluoromethyl and/or —Z— R groups, Z is —O—, —S— or —SO— and R is alkyl, alkenyl, alkynyl or cyanomethyl, the alkyl, alkenyl and alkynyl groups each having up to 5 C atoms, or a physiologically acceptable salt thereof.

These compounds encompass 1,3,4,7-tetraazaindenes (imidazo(4,5-b)pyrazines; cf. "The Ring Index", 2nd Edition, American Chemical Society, 1960, No. 1176; formula Ia) and 1,3,5,6-tetraazaindenes (imidazo(4,5-d)pyridazines; cf. "The Ring Index", l.c., No. 1177; formula Ib):

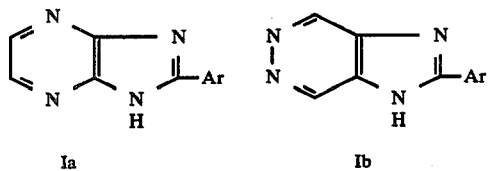

Ia                                    Ib

German Offenlegungsschrift No. 2,305,339 discloses similar compounds.

SUMMARY

An object of an aspect of this invention is to provide new compounds.

According to an aspect of another object, such compounds are formulated into pharmaceutical compositions.

According to an aspect of another object of this invention, there are provided methods of therapeutically treating mammals having various disorders.

Upon further study of the specification and appended claims, further objects and advantages of this invention will become apparent to those skilled in the art.

These aspects are attained by providing compounds of the above formula I and their physiologically acceptable salts.

These compounds combine good tolerance with valuable pharmacological properties. They have, in particular, an effect on the blood pressure, the force of myocardial contraction (positive inotropic effect) and an anti-ulcer effect. The effect on the blood pressure and the heart can be determined, for example, on anaesthetized or conscious dogs, cats, monkeys or minipigs, and the positive inotropic effect also on isolated heart preparations (for example atrium, papillary muscle or perfused whole heart) of rats, guineapigs or cats, for example using methods as described in Arzneimittelforschung, Volume 31 (I) No. 1a (1981), pages 141 to 170.

The compounds can therefore be used as active medical compounds in human and veterinary medicine. They can also be used as intermediates to prepare each other as well as to prepare other known active medical compounds by conventional methods.

In the compounds of the formula I, the phenyl group can be monosubstituted (in o-, m- or p-position), disubstituted (in 2,3-, 2,4-, 2,5-, 2,6-, 3,4- or 3,5-position) or trisubstituted (in 2,3,4-, 2,3,5-, 2,3,6- or 3,4,5-position). The radical Ar is preferably a 2,4-disubstituted or an o- or p-monosubstituted phenyl group.

Alkyl is preferably unbranched, preferably has 1 to 4, in particular 1 to 3, C atoms, and preferably is methyl, but also ethyl, propyl, isopropyl, butyl, isobutyl, sec.-butyl, tert.-butyl, pentyl or isopentyl.

Alkenyl is preferably unbranched, has in particular 2 to 4, preferably 3, C atoms, and preferably is allyl, but also vinyl, 1-propen-1-yl, butenyl, such as 1-buten-1-yl, 2-buten-1-yl, 3-buten-1-yl, pentenyl, such as 1-penten-1-yl, 2-penten-1-yl or 3-penten-1-yl. However, the alkenyl groups can also be branched; examples thereof are arelmethyl-2-propen-1-yl, 1-methyl-2-buten-1-yl, 2-methyl-3-buten-1-yl and 1,1-dimethyl-2-propen-1-yl.

Preferably alkynyl groups are unbranched and have, in particular, 3 or even, 2, 4 or 5 C atoms, such as propargyl (=2-propyn-1-yl), but also ethynyl, 1-propyn-1-yl, butynyl, such as 1-butyn-1-yl, 2-butyn-1-yl or 3-butyn-1-yl or pentynyl, such as 1-pentyn-1-yl, 2-pentyn-1-yl or 3-pentyn-1-yl. However, the alkynyl groups can also be branched; examples thereof are 1-methyl-2-propyn-1-yl, 1-methyl-2-butyn-1-yl, 2-methyl-3-butyn-1-yl and 1,1-dimethyl-2-propyn-1-yl.

Examples of substituents which are particularly preferable on the phenyl radical in compounds of the formula I are methoxy, propargyloxy, cyanomethoxy; but also hydroxyl, mercapto, dimethylamino, diethylamino, trifluoromethyl, ethoxy, propoxy, isopropoxy,, butoxy, vinyloxy, allyloxy, methylthio, ethylthio, propylthio, isopropylthio, butylthio, vinylthio, allylthio, propargylthio, cyanomethylthio, methylsulfinyl, ethylsulfinyl, propylsulfinyl, isopropylsulfinyl, butylsulfinyl, vinylsulfinyl, allylsulfinyl, propargylsulfinyl and cyanomethylsulfinyl.

The invention relates particularly to those compounds of the formula I in which at least one of the radicals mentioned has one of the abovementioned preferable meanings. Some preferable groups of compounds can be represented by the subformulae Ic and Id, below, which correspond to the formula I and in which the radical Ar is a phenyl radical which in Ic: is unsubstituted or substituted by 1-3 alkoxy groups and/or a trifluoromethyl, alkenyloxy, alkynyloxy, alkylthio or cyanomethoxy group, the alkyl, alkenyl and alkynyl groups each having up to 3 C atoms; and in Id: is substituted by two methoxy groups or by one methoxy group and one propargyloxy or cyanomethoxy group.

Those compounds of the formula I or Ia to Id are particularly preferable in which the substituents are in 2- and/or 4-position.

The invention also relates to a process for preparing compounds of the formula I and their physiologically acceptable salts, characterized in that a diamine of the general formula II

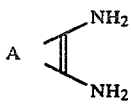

in which the group —A— is as defined above, is reacted with a benzoic acid of the general formula III HOOC—Ar     III in which Ar is as defined above, or with one of its reactive derivatives or with an aldehyde of the general formula IV OCH—Ar     IV in which Ar is as defined above, in the presence of an oxidizing agent, or that a compound which has the formula I but instead of one or more free hydroxyl and/or mercapto groups contains one or more protected hydroxyl and/or mercapto groups is treated with a solvolyzing or hydrogenolyzing agent, and that, if appropriate, the product obtained has its hydroxyl groups etherified and/or its mercapto groups converted into thioether groups and/or its thioether groups oxidized to sulfinyl groups and/or a compound obtained is converted into one of its physiologically acceptable salts by treating it with an acid.

Compounds of the formula I are otherwise prepared by methods known per se, as described in the literature (for example in the standard works such as Houben-Weyl, Methoden der Organischen Chemie [Methods of Organic Chemistry], Georg-Thieme-Verlag, Stuttgart; but in particular in German Offenlegungsschrift No. 2,305,339), and under reaction conditions which are known and suitable for the reactions mentioned, and it is also possible to use versions of methods which are known per se but which are not specifically mentioned here.

The starting materials, if desired, can also be formed in situ, namely by leaving them in the reaction mixture and immediately reacting them to yield compounds of the formula I. Alternatively, it is possible to carry out the reaction in stages, in which further intermediates can be isolated.

Compounds of the formula I are preferably obtained by reacting II with benzoic acids of the formula III or their reactive derivatives. Suitable for use as reactive derivatives are, in particular, the corresponding nitriles, acid halides, esters, amides, imidates, thioimidates, imidyl halides, amidines, thiocarboxylates, dithiocarboxylates or orthoesters.

Some of the starting materials II and III are known. Those which are not known can be prepared by methods which are known per se. For example, benzoic acids of the formula III which carry —Z—R groups can be obtained by etherifying corresponding hydroxybenzoic acids or by oxidizing corresponding benzoic acids which contain thioether groups; the etherification or thioetherification can also be carried out in stages.

In detail the reaction of II with III is carried out in the presence or absence of an inert solvent at temperatures between about −20° and about 250°, preferably between 60° and 150°. Examples of suitable solvents are hydrocarbons, such as benzene, toluene, xylenes or mesitylene, tertiary bases, such as triethylamine, pyridine or picolines, glycols and glycol ethers, such as ethylene glycol, diethylene glycol or 2-methoxyethanol, ketones, such as acetone, ethers, such as tetrahydrofuran or dioxane, amides, such as dimethylformamide, and sulfoxides, such as dimethyl sulfoxide. Mixtures of these solvents are also suitable. In some cases it is advisable to add catalytic amounts of an acid such as p-toluenesulfonic acid or to add a dehydrating agent, such as phosphorus oxychloride, polyphosphoric acid or thionyl chloride, and the dehydrating agent can also act as solvent.

If the free benzoic acids of the formula III are used, the reaction is preferably carried out in the presence of one of the dehydrating agents mentioned and, if appropriate, of a tertiary base, such as pyridine or triethylamine, preferably at temperatures between −20° and 150°.

The reaction can also be carried out in stages. For example, it is possible to partially acylate II with an acid chloride of the formula Ar—COCl to give 2-ArCONH-3-aminopyrazine or 3-ArCONH-4-aminopyridazine, which is then dehydrated, for example with $POCl_3$, to give I.

It is also possible to use instead of III a corresponding aldehyde of the formula IV provided the reaction is carried out in the presence of an oxidizing agent. The oxidizing agent preferably used is sulfur in a hydrocarbon, such as benzene, toluene, xylene or mesitylene, or sodium disulfite in solvents such as dimethylacetamine, either at temperatures between about 80° and about 200°. The aldehydes of the formula IV are generally new, and can be obtained, for example, by etherifying the corresponding hydroxyaldehydes.

Compounds of the formula I which contain free hydroxyl and/or mercapto groups can also be obtained by solvolysis or hydrogenolysis of corresponding compounds where the hydroxyl and/or mercapto groups are blocked by protective groups which can be split off in this way.

The starting materials for this solvolysis or hydrogenolysis have the general formula V

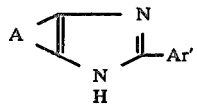

in which Ar' is a phenyl radical which is substituted by one to three protected hydroxyl and/or mercapto groups and can also carry one or two free hydroxyl, mercapto, dialkylamino, trifluoromethyl and/or Z—R groups, but which is at most trisubstituted, and A, Z and R have the above-mentioned meanings.

The starting materials of the formula V can be obtained, for example, by reacting II with a benzoicacid of the formula HOOC—Ar' or its reactive derivatives by the above-mentioned methods.

Suitable protective groups are the known "hydroxyl-protecting" groups and "mercapto-protecting" groups. These expressions relate to groups which are suitable for protecting hydroxyl or mercapto groups from chemical conversion but which are easily removable after the desired chemical reaction has been carried out elsewhere in the molecule. Examples of typical protective groups are readily cleavable ester, thioester, ether and thioether groups having preferably 1-12 C atoms, specific examples being alkanoyl having preferably 1-6 C atoms, such as acetyl, aroyl having preferably 7-11 C atoms, such as benzoyl, unsubstituted and substituted aryl and aralkyl each having up to 11 C atoms, such as 2,4-dinitrophenyl, benzyl or triphenylmethyl, and also, for example, tetrahydropyranyl. The type and size of the protective groups ae not critical, since they are split off in the present process.

The solvolytically detachable protective groups are preferably solvolyzed in a hydrolysis in an aqueous or aqueous-alcoholic medium in the presence of acids such as hydrochloric acid or bases such as sodium hydroxide or potassium hydroxide at temperatures between about 0° and 100°.

The hydrogenolytically detachable protective groups are hydrogenolyzed, for example, in the presence of a heavy metal catalyst, such as platinum, palladium or nickel, in an inert solvent such as methanol, ethanol, tetrahydrofuran or ethyl acetate, at temperatures between about 0° and 100° under pressures between about 1 and 200 bar.

If desired, one or more of the hydroxyl groups and/or mercapto groups present in the product can be etherified and converted into thioether groups respectively.

Suitable etherifying agents or thioetherifying agents are preferably those of the general formula VI $$X-R \qquad VI$$

in which X is Cl, Br, I, OH, alkylsulfonyloxy or arylsulfonyloxy and R is alkyl, alkenyl, alkynyl or cyanomethyl, the alkyl, alkenyl and alkynyl groups each having up to 5 and the aryl group having 6–10 C atoms.

Examples of typical etherifying or thioetherifying agents are methyl, ethyl, propyl, isopropyl, allyl or propargyl chloride or bromide, chloroacetonitrile and bromoacetonitrile.

In the etherification or thioetherification, the hydroxy compound or mercapto compound is preferably first converted into one of its salts, for example the Na salt, which is then reacted with VI in one of the specified solvents at temperatures between about 0° and 120°. It is also possible to etherify a free hydroxy compound VI (X=OH) in the presence of diethyl azodicarboxylate/triphenylphosphine, preferably in a solvent such as tetrahydrofuran or dioxane at temperatures between about 10° and about 40°.

It is also possible, if desired, to oxidize a thioether group which may be present in a product of the formula I into a sulfinyl group, preferably by means of hydrogen peroxide, peracids or Cr(VI) compounds, such as chromic acid, in the presence of an inert solvent such as water, an alcohol (for example methanol or ethanol), an acid (for example acetic acid) or a ketone (for example acetone) at temperatures between about −20° and 100°.

A base of the formula I can be converted with an acid into the corresponding acid addition salt. Suitable acids for this reaction are those which give physiologically acceptable salts. For instance, inorganic acids can be used, for example, sulfuric acid, nitric acid, hydrohalic acids, such as hydrochloric acid or hydrobromic acid, phosphoric acids, such as orthophosphoric acid, sulfamic acid, and also organic acids, in particular aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic acid, ethanesulfonic acid, ethanedisulfonic acid, 2-hydroxyethanesulfonic acid, benzenesulfonic acid, p-toluenesulfonic acid, naphthalenemonosulfonic acids, naphthalenedisulfonic acids, or laurylsulfuric acid.

The invention also relates to the use of compounds of the formula I and of their physiologically acceptable salts in the preparation of pharmaceutical preparations, in particular by non-chemical means. In this use, they can be brought into a suitable administration form together with at least one solid, liquid or semiliquid carrier or adjunct and, if appropriate, in combination with one or more other active ingredients.

The invention also relates to agents, in particular pharmaceutical preparations which contain at least one compound of the formula I and/or one of its physiologically acceptable salts.

These preparations can be used as medicaments in human or veterinary medicine. Suitable carriers are organic or inorganic substances which are suitable for enteral (for example oral), parenteral or topical application and which do not react with the new compounds, for example water, vegetable oils, benzyl alcohols, polyethylene glycols, glycerol triacetate, gelatin, carbohydrates such as lactose or starch, magnesium stearate, talc, or vaseline. Oral administration uses in particular tablets, coated tablets, capsules, syrups, juices or drops, rectal administration suppositories, parenteral administration solutions, preferably oily or aqueous solutions, and suspensions, emulsions or implants, and topical administration ointments, creams or powders. The new compounds can also be lyophilized and the resulting lyophilizates used, for example, in preparing injection preparations. The above-mentioned preparations can be sterilized and/or contain adjuncts, such as lubricants, preservatives, stabilizers and/or wetting agents, emulsifiers, salts to affect the osmotic pressure, buffer substances, colorants, flavorings and/or aromas. If desired, they can also contain one or more further active compounds, for example one or more vitamins.

The invention also relates to the use of compounds of the formula I in the treatment of diseases, in particular cardiac insufficiency, and to their use in the therapeutic treatment of the human or animal body.

When used in treatments, the substances according to the invention are as a rule administered in a manner similar to that of known positively inotropic active substances, such as Sulmazol or Amrinon, preferably in dosages between about 10 and 500 mg, in particular between 20 and 100 mg, per unit dose. The daily dose is preferably between 0.2 and 10 mg per kg of body weight. The specific dose for a particular patient, however, depends on various factors, for example on the effectiveness of the specific compound used, on his age, body weight, general state of health, sex, on the diet, on the time and method of administration, on the rate of excretion, on the combination of drugs, and on the severity of the particular illness at which the treatment is aimed. Oral application is preferable. Compared with the digitalis glycosides hitherto used in the treatment of cardiac insufficiency, the compounds of the formula I are distinguished by an improved therapeutic spectrum and peripheral relief.

In the examples which follow, "customary working up" denotes:

Water or dilute sodium hydroxide solution is added if necessary, the mixture is extracted with an organic solvent such as ethyl acetate, chloroform or dichloromethane, the phases are separated, the organic phase is dried over sodium sulfate, the sodium sulfate is filtered off, the filtrate is evaporated to dryness, and the residue is purified by chromatography and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

A mixture of 11 g of 2,3-diaminopyrazine (IIa), 20.6 g of 2-methoxy-4-propargyloxybenzoic acid [m.p. 142°; obtainable by reacting methyl 2,4-dihydroxybenzoate with propargyl chloride to give methyl 2-hydroxy-4-propargyloxybenzoate (m.p. 100°), reacting the latter with methyl iodide to give methyl 2-methoxy-4-propargyloxybenzoate (m.p. 88°), and hydrolysing the latter] and 300 ml of $POCl_3$ is boiled for 2 hours. The mixture is evaporated to dryness, ice-water is added to the residue, and the mixture is rendered alkaline with $K_2CO_3$ solution. The precipitated 2-(2-methoxy-4-propargyloxyphenyl)-1,3,4,7-tetraazaindene is filtered off. M.p. 189°-190°.

IIa or 3,4-diaminopyridazine (IIb) and the corresponding benzoic acids of the formula III (for example o-propargyloxybenzoic acid, m.p. 82°; m-propargyloxybenzoic acid, m.p. 130°; p-propargyloxybenzoic acid, m.p. 224°; 2-methoxy-5-propargyloxybenzoic acid, m.p. 103°; 3-methoxy-4-propargyloxybenzoic acid, m.p. 195°; 3,5-dimethoxy-4-propargyloxybenzoic acid, m.p. 208°; 2,4-bis-propargyloxybenzoic acid, m.p. 152°) give in a similar manner, and while the reaction temperatures are kept at between 70° and 110°:

2-phenyl-1,3,4,7-tetraazaindene, m.p. 286°-287°
2-o-hydroxyphenyl-1,3,4,7-tetraazaindene
2-m-hydroxyphenyl-1,3,4,7-tetraazaindene
2-p-hydroxyphenyl-1,3,4,7-tetraazaindene
2-o-mercaptophenyl-1,3,4,7-tetraazaindene
2-m-mercaptophenyl-1,3,4,7-tetraazaindene
2-p-mercaptophenyl-1,3,4,7-tetraazaindene
2-o-dimethylaminophenyl-1,3,4,7-tetraazaindene
2-m-dimethylaminophenyl-1,3,4,7-tetraazaindene
2-p-dimethylaminophenyl-1,3,4,7-tetraazaindene
2-o-diethylaminophenyl-1,3,4,7-tetraazaindene
2-m-diethylaminophenyl-1,3,4,7-tetraazaindene
2-p-diethylaminophenyl-1,3,4,7-tetraazaindene
2-o-trifluoromethylphenyl-1,3,4,7-tetraazaindene
2-m-trifluoromethylphenyl-1,3,4,7-tetraazaindene
2-p-trifluoromethylphenyl-1,3,4,7-tetraazaindene, m.p. 338°
2-o-methoxyphenyl-1,3,4,7-tetraazaindene, m.p. 165°
2-m-methoxyphenyl-1,3,4,7-tetraazaindene
2-p-methoxyphenyl-1,3,4,7-tetraazaindene, m.p. 289°
2-o-ethoxyphenyl-1,3,4,7-tetraazaindene
2-m-ethoxyphenyl-1,3,4,7-tetraazaindene
2-p-ethoxyphenyl-1,3,4,7-tetraazaindene
2-o-propoxyphenyl-1,3,4,7-tetraazaindene
2-m-propoxyphenyl-1,3,4,7-tetraazaindene
2-p-propoxyphenyl-1,3,4,7-tetraazaindene
2-p-isopropoxyphenyl-1,3,4,7-tetraazaindene
2-p-butoxyphenyl-1,3,4,7-tetraazaindene
2-p-isobutoxyphenyl-1,3,4,7-tetraazaindene
2-p-pentoxyphenyl-1,3,4,7-tetraazaindene
2-o-allyloxyphenyl-1,3,4,7-tetraazaindene
2-m-allyloxyphenyl-1,3,4,7-tetraazaindene
2-p-allyloxyphenyl-1,3,4,7-tetraazaindene
2-p-ethynyloxyphenyl-1,3,4,7-tetraazaindene
2-o-propargyloxyphenyl-1,3,4,7-tetraazaindene
2-m-propargyloxyphenyl-1,3,4,7-tetraazaindene
2-p-propargyloxyphenyl-1,3,4,7-tetraazaindene, fumarate, m.p. 273°
2-(p-3-pentyn-1-yloxyphenyl)--1,3,4,7-tetraazaindene
2-o-cyanomethoxyphenyl-1,3,4,7-tetraazaindene
2-m-cyanomethoxyphenyl-1,3,4,7-tetraazaindene
2-p-cyanomethoxyphenyl-1,3,4,7-tetraazaindene
2-o-methylthiophenyl-1,3,4,7-tetraazaindene
2-m-methylthiophenyl-1,3,4,7-tetraazaindene
2-p-methylthiophenyl-1,3,4,7-tetraazaindene
2-o-ethylthiophenyl-1,3,4,7-tetraazaindene
2-m-ethylthiophenyl-1,3,4,7-tetraazaindene
2-p-ethylthiophenyl-1,3,4,7-tetraazaindene
2-o-propylthiophenyl-1,3,4,7-tetraazaindene
2-m-propylthiophenyl-1,3,4,7-tetraazaindene
2-p-propylthiophenyl-1,3,4,7-tetraazaindene
2-p-isopropylthiophenyl-1,3,4,7-tetraazaindene
2-p-butylthiophenyl-1,3,4,7-tetraazaindene
2-p-isobutylthiophenyl-1,3,4,7-tetraazaindene
2-p-pentylthiophenyl-1,3,4,7-tetraazaindene
2-o-allylthiophenyl-1,3,4,7-tetraazaindene
2-m-allylthiophenyl-1,3,4,7-tetraazaindene
2-p-allylthiophenyl-1,3,4,7-tetraazaindene
2-p-ethynylthiophenyl-1,3,4,7-tetraazaindene
2-o-propargylthiophenyl-1,3,4,7-tetraazaindene
2-m-propargylthiophenyl-1,3,4,7-tetraazaindene
2-p-propargylthiophenyl-1,3,4,7-tetraazaindene
2-o-cyanomethylthiophenyl-1,3,4,7-tetraazaindene
2-m-cyanomethylthiophenyl-1,3,4,7-tetraazaindene
2-p-cyanomethylthiophenyl-1,3,4,7-tetraazaindene
2-o-methylsulfinylphenyl-1,3,4,7-tetraazaindene
2-m-methylsulfinylphenyl-1,3,4,7-tetraazaindene
2-p-methylsulfinylphenyl-1,3,4,7-tetraazaindene
2-o-ethylsulfinylphenyl-1,3,4,7-tetraazaindene
2-m-ethylsulfinylphenyl-1,3,4,7-tetraazaindene
2-p-ethylsulfinylphenyl-1,3,4,7-tetraazaindene
2-o-propylsulfinylphenyl-1,3,4,7-tetraazaindene
2-m-propylsulfinylphenyl-1,3,4,7-tetraazaindene
2-p-propylsulfinylphenyl-1,3,4,7-tetraazaindene
2-p-isopropylsulfinylphenyl-1,3,4,7-tetraazaindene
2-p-butylsulfinylphenyl-1,3,4,7-tetraazaindene
2-p-isobutylsulfinylphenyl-1,3,4,7-tetraazaindene
2-p-pentylsulfinylphenyl-1,3,4,7-tetraazaindene
2-o-allylsulfinylphenyl-1,3,4,7-tetraazaindene
2-m-allylsulfinylphenyl-1,3,4,7-tetraazaindene
2-p-allylsulfinylphenyl-1,3,4,7-tetraazaindene
2-p-ethynylsulfinylphenyl-1,3,4,7-tetraazaindene
2-o-propargylsulfinylphenyl-1,3,4,7-tetraazaindene
2-m-propargylsulfinylphenyl-1,3,4,7-tetraazaindene
2-p-propargylsulfinylphenyl-1,3,4,7-tetraazaindene
2-o-cyanomethylsulfinylphenyl-1,3,4,7-tetraazaindene
2-m-cyanomethylsulfinylphenyl-1,3,4,7-tetraazaindene
2-p-cyanomethylsulfinylphenyl-1,3,4,7-tetraazaindene
2-(2,4-dihydroxyphenyl)-1,3,4,7-tetraazaindene
2-(2-hydroxy-4-methoxyphenyl)-1,3,4,7-tetraazaindene 2-(4-hydroxy-2-methoxyphenyl)-1,3,4,7-tetraazaindene
3-(2-ethoxy-4-hydroxyphenyl)-1,3,4,7-tetraazaindene
2-(4-ethoxy-2-hydroxyphenyl)-1,3,4,7-tetraazaindene
2-(2-dimethylamino-4-methoxyphenyl)-1,3,4,7-tetraazaindene
2-(4-dimethylamino-2-methoxyphenyl)-1,3,4,7-tetraazaindene, m.p. 279°-280°
2-(2-methoxy-4-trifluoromethylphenyl)-1,3,4,7-tetraazaindene
2-(4-methoxy-2-trifluoromethylphenyl)-1,3,4,7-tetraazaindene
2-(2,3-dimethoxyphenyl)-1,3,4,7-tetraazaindene
2-(2,4-dimethoxyphenyl)-1,3,4,7-tetraazaindene, m.p. 210°-215°; fumarate, m.p. 265° (decomposition)
2-(2,5-dimethoxyphenyl)-1,3,4,7-tetraazaindene
2-(2,6-dimethoxyphenyl)-1,3,4,7-tetraazaindene
2-(3,4-dimethoxyphenyl)-1,3,4,7-tetraazaindene, m.p. 248°-249°
2-(3,5-dimethoxyphenyl)-1,3,4,7-tetraazaindene
2-(2-ethoxy-4-methoxyphenyl)-1,3,4,7-tetraazaindene
2-(4-ethoxy-2-methoxyphenyl)-1,3,4,7-tetraazaindene
2-(2,4-diethoxyphenyl)-1,3,4,7-tetraazaindene
2-(2-isopropoxy-4-methoxyphenyl)-1,3,4,7-tetraazaindene
2-(4-isopropoxy-2-methoxyphenyl)-1,3,4,7-tetraazaindene
2-(2,4-diisopropoxyphenyl)-1,3,4,7-tetraazaindene
2-(2-allyloxy-4-methoxyphenyl)-1,3,4,7-tetraazaindene
2-(4-allyloxy-2-methoxyphenyl)-1,3,4,7-tetraazaindene
2-(2,4-diallyloxyphenyl)-1,3,4,7-tetraazaindene
2-(2-hydroxy-4-propargyloxyphenyl)-1,3,4,7-tetraazaindene
2-(4-hydroxy-2-propargyloxyphenyl)-1,3,4,7-tetraazaindene
2-(2-methoxy-3-propargyloxyphenyl)-1,3,4,7-tetraazaindene
2-(2-methoxy-5-propargyloxyphenyl)-1,3,4,7-tetraazaindene
2-(2-methoxy-6-propargyloxyphenyl)-1,3,4,7-tetraazaindene
2-(3-methoxy-4-propargyloxyphenyl)-1,3,4,7-tetraazaindene
2-(4-methoxy-2-propargyloxyphenyl)-1,3,4,7-tetraazaindene
2-(2-ethoxy-4-propargyloxyphenyl)-1,3,4,7-tetraazaindene
2-(4-ethoxy-2-propargyloxyphenyl)-1,3,4,7-tetraazaindene
2-(2-allyloxy-4-propargyloxyphenyl)-1,3,4,7-tetraazaindene
2-(4-allyloxy-2-propargyloxyphenyl)-1,3,4,7-tetraazaindene
2-(2,4-dipropargyloxyphenyl)-1,3,4,7-tetraazaindene
2-(2-cyanomethoxy-4-hydroxyphenyl)-1,3,4,7-tetraazaindene
2-(4-cyanomethoxy-2-hydroxyphenyl)-1,3,4,7-tetraazaindene 2-(2-cyanomethoxy-4-methoxyphenyl)-1,3,4,7-tetraazaindene 2-(4-cyanomethoxy-2-methoxyphenyl)-1,3,4,7-tetraazaindene, m.p. 232°-233°.
2-(2-cyanomethoxy-4-ethoxyphenyl)-1,3,4,7-tetraazaindene
2-(4-cyanomethoxy-2-ethoxyphenyl)-1,3,4,7-tetraazaindene
2-(2-allyloxy-4-cyanomethoxyphenyl)-1,3,4,7-tetraazaindene
2-(4-allyloxy-2-cyanomethoxyphenyl)-1,3,4,7-tetraazaindene
2-(2-cyanomethoxy-4-propargyloxyphenyl)-1,3,4,7-tetraazaindene
2-(4-cyanomethoxy-2-propargyloxyphenyl)-1,3,4,7-tetraazaindene
2-(2,4-bis-cyanomethoxyphenyl)-1,3,4,7-tetraazaindene
2-(2-mercapto-4-methoxyphenyl)-1,3,4,7-tetraazaindene
2-(4-mercapto-2-methoxyphenyl)-1,3,4,7-tetraazaindene
2-(2-hydroxy-4-methylthiophenyl)-1,3,4,7-tetraazaindene
2-(4-hydroxy-2-methylthiophenyl)-1,3,4,7-tetraazaindene
2-(2-methoxy-4-methylthiophenyl)-1,3,4,7-tetraazaindene, m.p. 198°
2-(2-methoxy-5-methylthiophenyl)-1,3,4,7-tetraazaindene
2-(4-methoxy-2-methylthiophenyl)-1,3,4,7-tetraazaindene
2-(2-ethoxy-4-methylthiophenyl)-1,3,4,7-tetraazaindene
2-(4-ethoxy-2-methylthiophenyl)-1,3,4,7-tetraazaindene
2-(2-allyloxy-4-methylthiophenyl)-1,3,4,7-tetraazaindene
2-(4-allyloxy-2-methylthiophenyl)-1,3,4,7-tetraazaindene
2-(2-methylthio-4-propargyloxyphenyl)-1,3,4,7-tetraazaindene
2-(4-methylthio-2-propargyloxyphenyl)-1,3,4,7-tetraazaindene
2-(2-cyanomethoxy-4-methylthiophenyl)-1,3,4,7-tetraazaindene
2-(4-cyanomethoxy-2-methylthiophenyl)-1,3,4,7-tetraazaindene
2-(2,4-bis-methylthiophenyl)-1,3,4,7-tetraazaindene
2-(4-ethylthio-2-methoxyphenyl)-1,3,4,7-tetraazaindene
2-(4-allylthio-2-methoxyphenyl)-1,3,4,7-tetraazaindene
2-(4-methoxy-2-propargylthiophenyl)-1,3,4,7-tetraazaindene
2-(4-cyanomethylthio-2-methoxyphenyl)-1,3,4,7-tetraazaindene, m.p. 204°-205°
2-(2-hydroxy-4-methylsulfinylphenyl)-1,3,4,7-tetraazaindene
2-(4-hydroxy-2-methylsulfinylphenyl)-1,3,4,7-tetraazaindene
2-(2-methoxy-4-methylsulfinylphenyl)-1,3,4,7-tetraazaindene
2-(4-methoxy-2-methylsulfinylphenyl)-1,3,4,7-tetraazaindene
2-(2-ethoxy-4-methylsulfinylphenyl)-1,3,4,7-tetraazaindene
2-(4-ethoxy-2-methylsulfinylphenyl)-1,3,4,7-tetraazaindene
2-(2-allyloxy-4-methylsulfinylphenyl)-1,3,4,7-tetraazaindene
2-(4-allyloxy-2-methylsulfinylphenyl)-1,3,4,7-tetraazaindene
2-(2-methylsulfinyl-4-propargyloxyphenyl)-1,3,4,7-tetraazaindene 2-(4-methylsulfinyl-2-propargyloxyphenyl)-1,3,4,7-tetraazaindene
2-(2-cyanomethoxy-4-methylsulfinylphenyl)-1,3,4,7-tetraazaindene
2-(4-cyanomethoxy-2-methylsulfinylphenyl)-1,3,4,7-tetraazaindene
2-(2,4-bis-methylsulfinylphenyl)-1,3,4,7-tetraazaindene
2-(4-ethylsulfinyl-2-methoxyphenyl)-1,3,4,7-tetraazaindene
2-(4-allylsulfinyl-2-methoxyphenyl)-1,3,4,7-tetraazaindene
2-(2-methoxy-4-propargylsulfinyl)-1,3,4,7-tetraazaindene
2-(4-cyanomethylsulfinyl-2-methoxy)-1,3,4,7-tetraazaindene
2-(2,3,4-trimethoxyphenyl)-1,3,4,7-tetraazaindene, m.p. 216°
2-(3,4,5-trimethoxyphenyl)-1,3,4,7-tetraazaindene
2-(3,5-dimethoxy-4-propargyloxyphenyl)-1,3,4,7-tetraazaindene
2-phenyl-1,3,5,6-tetraazaindene
2-o-hydroxyphenyl-1,3,5,6-tetraazaindene
2-m-hydroxyphenyl-1,3,5,6-tetraazaindene
2-p-hydroxyphenyl-1,3,5,6-tetraazaindene
2-o-mercaptophenyl-1,3,5,6-tetraazaindene
2-m-mercaptophenyl-1,3,5,6-tetraazaindene
2-p-mercaptophenyl-1,3,5,6-tetraazaindene
2-o-dimethylaminophenyl-1,3,5,6-tetraazaindene
2-m-dimethylaminophenyl-1,3,5,6-tetraazaindene
2-p-dimethylaminophenyl-1,3,5,6-tetraazaindene
2-o-diethylaminophenyl-1,3,5,6-tetraazaindene
2-m-diethylaminophenyl-1,3,5,6-tetraazaindene
2-p-diethylaminophenyl-1,3,5,6-tetraazaindene
2-o-trifluoromethylphenyl-1,3,5,6-tetraazaindene
2-m-trifluoromethylphenyl-1,3,5,6-tetraazaindene
2-p-trifluoromethylphenyl-1,3,5,6-tetraazaindene
2-o-methoxyphenyl-1,3,5,6-tetraazaindene, m.p. 208°
2-m-methoxyphenyl-1,3,5,6-tetraazaindene
2-p-methoxyphenyl-1,3,5,6-tetraazaindene
2-o-ethoxyphenyl-1,3,5,6-tetraazaindene
2-m-ethoxyphenyl-1,3,5,6-tetraazaindene
2-p-ethoxyphenyl-1,3,5,6-tetraazaindene
2-o-propoxyphenyl-1,3,5,6-tetraazaindene
2-m-propoxyphenyl-1,3,5,6-tetraazaindene
2-p-propoxyphenyl-1,3,5,6-tetraazaindene
2-p-isopropoxyphenyl-1,3,5,6-tetraazaindene
2-p-butoxyphenyl-1,3,5,6-tetraazaindene
2-p-isobutoxyphenyl-1,3,5,6-tetraazaindene
2-p-pentoxyphenyl-1,3,5,6-tetraazaindene
2-o-allyloxyphenyl-1,3,5,6-tetraazaindene
2-m-allyloxyphenyl-1,3,5,6-tetraazaindene
2-p-allyloxyphenyl-1,3,5,6-tetraazaindene
2-ethynyloxyphenyl-1,3,5,6-tetraazaindene
2-o-propargyloxyphenyl-1,3,5,6-tetraazaindene
2-m-propargyloxyphenyl-1,3,5,6-tetraazaindene
2-p-propargyloxyphenyl-1,3,5,6-tetraazaindene
2-(p-3-pentyn-1-yloxyphenyl)-1,3,5,6-tetraazaindene
2-o-cyanomethoxyphenyl-1,3,5,6-tetraazaindene
2-m-cyanomethoxyphenyl-1,3,5,6-tetraazaindene
2-p-cyanomethoxyphenyl-1,3,5,6-tetraazaindene
2-o-methylthiophenyl-1,3,5,6-tetraazaindene
2-m-methylthiophenyl-1,3,5,6-tetraazaindene
2-p-methylthiophenyl-1,3,5,6-tetraazaindene
2-o-ethylthiophenyl-1,3,5,6-tetraazaindene
2-m-ethylthiophenyl-1,3,5,6-tetraazaindene
2-p-ethylthiophenyl-1,3,5,6-tetraazaindene
2-o-propylthiophenyl-1,3,5,6-tetraazaindene
2-m-propylthiophenyl-1,3,5,6-tetraazaindene
2-p-propylthiophenyl-1,3,5,6-tetraazaindene
2-p-isopropylthiophenyl-1,3,5,6-tetraazaindene
2-p-butylthiophenyl-1,3,5,6-tetraazaindene
2-p-isobutylthiophenyl-1,3,5,6-tetraazaindene
2-p-pentylthiophenyl-1,3,5,6-tetraazaindene
2-o-allylthiophenyl-1,3,5,6-tetraazaindene
2-m-allylthiophenyl-1,3,5,6-tetraazaindene
2-p-allylthiophenyl-1,3,5,6-tetraazaindene
2-p-ethynythiophenyl-1,3,5,6-tetraazaindene
2-o-propargylthiophenyl-1,3,5,6-tetraazaindene
2-m-propargylthiophenyl-1,3,5,6-tetraazaindene
2-p-propargylthiophenyl-1,3,5,6-tetraazaindene
2-o-cyanomethylthiophenyl-1,3,5,6-tetraazaindene
2-m-cyanomethylthiophenyl-1,3,5,6-tetraazaindene
2-p-cyanomethylthiophenyl-1,3,5,6-tetraazaindene
2-o-methylsulfinylphenyl-1,3,5,6-tetraazaindene
2-m-methylsulfinylphenyl-1,3,5,6-tetraazaindene
2-p-methylsulfinylphenyl-1,3,5,6-tetraazaindene
2-o-ethylsulfinylphenyl-1,3,5,6-tetraazaindene
2-m-ethylsulfinylphenyl-1,3,5,6-tetraazaindene
2-p-ethylsulfinylphenyl-1,3,5,6-tetraazaindene
2-o-propylsulfinylphenyl-1,3,5,6-tetraazaindene
2-m-propylsulfinylphenyl-1,3,5,6-tetraazaindene
2-p-propylsulfinylphenyl-1,3,5,6-tetraazaindene
2-p-isopropylsulfinylphenyl-1,3,5,6-tetraazaindene
2-p-butylsulfinylphenyl-1,3,5,6-tetraazaindene
2-p-isobutylsulfinylphenyl-1,3,5,6-tetraazaindene
2-p-pentylsulfinylphenyl-1,3,5,6-tetraazaindene
2-o-allylsulfinylphenyl-1,3,5,6-tetraazaindene
2-m-allylsulfinylphenyl-1,3,5,6-tetraazaindene
2-p-allylsulfinylphenyl-1,3,5,6-tetraazaindene
2-p-ethynylsulfinylphenyl-1,3,5,6-tetraazaindene
2-o-propargylsulfinylphenyl-1,3,5,6-tetraazaindene
2-m-propargylsulfinylphenyl-1,3,5,6-tetraazaindene
2-p-propargylsulfinylphenyl-1,3,5,6-tetraazaindene
2-o-cyanomethylsulfinylphenyl-1,3,5,6-tetraazaindene
2-m-cyanomethylsulfinylphenyl-1,3,5,6-tetraazaindene
2-p-cyanomethylsulfinylphenyl-1,3,5,6-tetraazaindene
2-(2,4-dihydroxyphenyl)-1,3,5,6-tetraazaindene
2-(2-hydroxy-4-methoxyphenyl)-1,3,5,6-tetraazaindene
2-(4-hydroxy-2-methoxyphenyl)-1,3,5,6-tetraazaindene
3-(2-ethoxy-4-hydroxyphenyl)-1,3,5,6-tetraazaindene
2-(4-ethoxy-2-hydroxyphenyl)-1,3,5,6-tetraazaindene
2-(2-dimethylamino-4-methoxyphenyl)-1,3,5,6-tetraazaindene
2-(4-dimethylamino-2-methoxyphenyl)-1,3,5,6-tetraazaindene fumarate, m.p. 226°
2-(2-methoxy-4-trifluoromethylphenyl)-1,3,5,6-tetraazaindene
2-(4-methoxy-2-trifluoromethylphenyl)-1,3,5,6-tetraazaindene
2-(2,3-dimethoxyphenyl)-1,3,5,6-tetraazaindene
2-(2,4-dimethoxyphenyl)-1,3,5,6-tetraazaindene, m.p. 268°
2-(2,5-dimethoxyphenyl)-1,3,5,6-tetraazaindene, hydrochloride, m.p. 290°
2-(2,6-dimethoxyphenyl)-1,3,5,6-tetraazaindene
2-(3,4-dimethoxyphenyl)-1,3,5,6-tetraazaindene, hydrochloride, m.p. 207°
2-(3,5-dimethoxyphenyl)-1,3,5,6-tetraazaindene
2-(2-ethoxy-4-methoxyphenyl)-1,3,5,6-tetraazaindene
2-(4-ethoxy-2-methoxyphenyl)-1,3,5,6-tetraazaindene 2-(2,4-diethoxyphenyl)-1,3,5,6-tetraazaindene
2-(2-isopropoxy-4-methoxyphenyl)-1,3,5,6-tetraazaindene
2-(4-isopropoxy-2-methoxyphenyl)-1,3,5,6-tetraazaindene
2-(2,4-diisopropoxyphenyl)-1,3,5,6-tetraazaindene
2-(2-allyloxy-4-methoxyphenyl)-1,3,5,6-tetraazaindene
2-(4-allyloxy-2-methoxyphenyl)-1,3,5,6-tetraazaindene, hydrochloride, m.p. 271°
2-(4-allyloxy-3-methoxyphenyl)-1,3,5,6-tetraazaindene, hydrochloride, m.p. 280°
2-(2,4-diallyloxyphenyl)-1,3,5,6-tetraazaindene
2-(2-hydroxy-4-propargyloxyphenyl)-1,3,5,6-tetraazaindene
2-(4-hydroxy-2-propargyloxyphenyl)-1,3,5,6-tetraazaindene
2-(2-methoxy-3-propargyloxyphenyl)-1,3,5,6-tetraazaindene
2-(2-methoxy-4-propargyloxyphenyl)-1,3,5,6-tetraazaindene, m.p. 224°
2-(2-methoxy-5-propargyloxyphenyl)-1,3,5,6-tetraazaindene
2-(2-methoxy-6-propargyloxyphenyl)-1,3,5,6-tetraazaindene
2-(3-methoxy-4-propargyloxyphenyl)-1,3,5,6-tetraazaindene, hydrochloride, m.p. 259°
2-(4-methoxy-2-propargyloxyphenyl)-1,3,5,6-tetraazaindene
2-(2-ethoxy-4-propargyloxyphenyl)-1,3,5,6-tetraazaindene
2-(4-ethoxy-2-propargyloxyphenyl)-1,3,5,6-tetraazaindene
2-(2-allyloxy-4-propargyloxyphenyl)-1,3,5,6-tetraazaindene
2-(4-allyloxy-2-propargyloxyphenyl)-1,3,5,6-tetraazaindene
2-(2,4-dipropargyloxyphenyl)-1,3,5,6-tetraazaindene, hydrochloride, m.p. 265°
2-(2-cyanomethoxy-4-hydroxyphenyl)-1,3,5,6-tetraazaindene
2-(4-cyanomethoxy-2-hydroxyphenyl)-1,3,5,6-tetraazaindene
2-(2-cyanomethoxy-4-methoxyphenyl)-1,3,5,6-tetraazaindene
2-(4-cyanomethoxy-2-methoxyphenyl)-1,3,5,6-tetraazaindene hydrochloride, m.p. 268°
2-(2-cyanomethoxy-4-ethoxyphenyl)-1,3,5,6-tetraazaindene
2-(4-cyanomethoxy-2-ethoxyphenyl)-1,3,5,6-tetraazaindene
2-(2-allyloxy-4-cyanomethoxyphenyl)-1,3,5,6-tetraazaindene
2-(4-allyloxy-2-cyanomethoxyphenyl)-1,3,5,6-tetraazaindene
2-(2-cyanomethoxy-4-propargyloxyphenyl)-1,3,5,6-tetraazaindene
2-(4-cyanomethoxy-2-propargyloxyphenyl)-1,3,5,6-tetraazaindene
2-(2,4-bis-cyanomethoxyphenyl)-1,3,5,6-tetraazaindene
2-(2-mercapto-4-methoxyphenyl)-1,3,5,6-tetraazaindene
2-(2-mercapto-2-methoxyphenyl)-1,3,5,6-tetraazaindene
2-(2-hydroxy-4-methylthiophenyl)-1,3,5,6-tetraazaindene
2-(4-hydroxy-2-methylthiophenyl)-1,3,5,6-tetraazaindene
2-(2-methoxy-4-methylthiophenyl)-1,3,5,6-tetraazaindene hydrochloride, m.p. 271°
2-(2-methoxy-5-methylthiophenyl)-1,3,5,6-tetraazaindene
2-(4-methoxy-2-methylthiophenyl)-1,3,5,6-tetraazaindene
2-(2-ethoxy-4-methylthiophenyl)-1,3,5,6-tetraazaindene
2-(4-ethoxy-2-methylthiophenyl)-1,3,5,6-tetraazaindene
2-(2-allyloxy-4-methylthiophenyl)-1,3,5,6-tetraazaindene
2-(4-allyloxy-2-methylthiophenyl)-1,3,5,5-tetraazaindene
2-(2-methylthio-4-propargyloxyphenyl)-1,3,5,6-tetraazaindene
2-(4-methylthio-2-propargyloxyphenyl)-1,3,5,6-tetraazaindene
2-(2-cyanomethoxy-4-methylthiophenyl)-1,3,5,6-tetraazaindene
2-(4-cyanomethoxy-2-methylthiophenyl)-1,3,5,6-tetraazaindene
2-(2,4-bis-methylthiophenyl)-1,3,5,6-tetraazaindene
2-(4-ethylthio-2-methoxyphenyl)-1,3,5,6-tetraazaindene, m.p. 248°
2-(4-allylthio-2-methoxyphenyl)-1,3,5,6-tetraazaindene
2-(2-methoxy-4-proparylthiophenyl)-1,3,5,6-tetraazaindene, m.p. 222°
2(4-cyanomethylthio-2-methoxyphenyl)-1,3,5,6-tetraazaindene, m.p. 240°
2-(2-hydroxy-4-methylsulfinylphenyl)-1,3,5,6-tetraazaindene
2-(4-hydroxy-2-methylsulfinylphenyl)-1,3,5,6-tetraazaindene
2-(2-methoxy-4-methylsulfinylphenyl)-1,3,5,6-tetraazaindene
2-(4-methoxy-2-methylsulfinylphenyl)-1,3,5,6-tetraazaindene
2-(2-ethoxy-4-methylsulfinylphenyl)-1,3,5,6-tetraazaindene
2-(2-ethoxy-2-methylsulfinylphenyl)-1,3,5,6-tetraazaindene
2-(2-allyloxy-4-methylsulfinylphenyl)-1,3,5,6-tetraazaindene
2-(4-allyloxy-2-methylsulfinylphenyl)-1,3,5,6-tetraazaindene
2-(2-methylsulfinyl-4-propargyloxyphenyl)-1,3,5,6-tetraazaindene
2-(4-methylsulfinyl-2-propargyloxyphenyl)-1,3,5,6-teraazaindene
2-(2-cyanomethoxy-4-methylsulfinylphenyl)-1,3,5,6-tetraazaindene
2-(4-cyanomethoxy-2-methylsulfinylphenyl)-1,3,5,6-tetraazaindene
2-(2,4-bis-methylsulfinylphenyl)-1,3,5,6-tetraazaindene
2-(4-ethylsulfinyl-2-methoxyphenyl)-1,3,5,6-tetraazaindene
2-(4-allylsulfinyl-2-methoxyphenyl)-1,3,5,6-tetraazaindene
2-(2-methoxy-4-propargylsulfinyl)-1,3,5,6-tetraazaindene
2-(4-cyanomethylsulfinyl-2-methoxy)-1,3,5,6-tetraazaindene
2-(2,3,4-trimethoxyphenyl)-1,3,5,6-tetraazaindene 2-(3,4,5-trimethoxyphenyl)-1,3,5,6-tetraazaindene
2-(3,5-dimethoxy-4-propargyloxyphenyl)-1,3,5,6-tetraazaindene.

EXAMPLE 2

A solution of 176 mg of p-propargyloxybenzoic acid in 1 ml of pyridine is mixed with a solution of 109 mg of IIa in 1 ml of pyridine, and the corresponding salt precipitates. 0.19 ml of $SOCl_2$ is added at 0° dropwise with stirring, the mixture is stirred at 0° for 1 hour and at 70° for 1 hour and evaporated to dryness, and the residue is taken up in dilute hydrochloric acid. The resulting hydrochloride is added to sodium carbonate solution, and the precipitated 2-p-propargyloxyphenyl-1,3,4,7-tetraazaindene is filtered off. Fumarate, m.p. 273°.

EXAMPLE 3

2.06 g of 2-methoxy-4-propargyloxybenzoic acid are boiled together with 7 ml of benzene and 4 ml of $SOCl_2$ for 1 hour, the mixture is evaporated to dryness, and the residue is dissolved in 5 ml of benzene. The solution of the acid chloride is added dropwise to a mixture of 1.1 g of IIb, 7 ml of pyridine and 5 ml of triethylamine. The resulting mixture is stirred at 20° for 2 hours, water is added, and the resulting mixture is neutralised with hydrochloric acid and worked up as customary. The 3-amino-4-(2-methoxy-4-propargyloxybenzoylamino)-pyridazine obtained is converted into the corresponding hydrochloride, and the latter (200 mg) is dissolved in 2 ml of pyridine. 0.2 ml of $POCl_3$ is added dropwise at 80° with stirring, the mixture is poured into water after 2 hours, and the resulting mixture is worked up as customary to give 2-(2-methoxy-4-propargyloxyphenyl)-1,3,5,6-tetraazaindene, m.p. 224°.

EXAMPLE 4

A mixture of 11 g of IIb, 19.6 g of methyl 2,4-dimethoxybenzoate and 300 ml of $POCl_3$ is heated at 120° for 2 hours, and evaporated to dryness, and the residue is treated with 2N hydrochloric acid. This gives 2-(2,4-dimethoxyphenyl)-1,3,5,6-tetraazaindene, m.p. 268°.

EXAMPLE 5

A mixture of 1.1 g of IIa, 1.63 g of 2,4-dimethoxybenzonitrile and 3 g of the monohydrate of p-toluenesulfonic acid is heated at 160° for 3.5 hours. After cooling down the mixture is worked up as customary to give 2-(2,4-dimethoxyphenyl)-1,3,4,7-tetraazaindene, m.p. 210°-215°.

EXAMPLE 6

A mixture of 4.33 g of S-methyl-2-methoxy-4-propargyloxythiobenzoic acid morpholide iodide (obtainable by boiling 2-methoxy-4-propargyloxybenzaldehyde with sulfur in morpholine and then reacting with $CH_3I$ in acetone), 1.1 g of IIb and 35 ml of ethylene glycol is heated at 130° for 40 minutes, and poured into ice-water, which is filtered to give 2-(2-methoxy-4-propargyloxyphenyl)-1,3,5,6-tetraazaindene, m.p. 224°.

EXAMPLE 7

1.1 g of IIb and 3 g of 2,4-dimethoxybenzoic anhydride are heated at 180° for 5 hours, then cooled down and worked up as customary to give 2-(2,4-dimethoxyphenyl)-1,3,5,6-tetraazaindene, m.p. 268°.

EXAMPLE 8

2.78 g of 2-methoxy-4-cyanomethoxybenzoic acid morpholide are mixed with 1.1 g of IIb, 5 ml of $POCl_3$ are added dropwise with stirring, and the mixture is boiled for 3 hours and evaporated to dryness. The customary working up gives 2-(4-cyanomethoxy-2-methoxyphenyl)-1,3,5,6-tetraazaindene, hydrochloride, m.p. 268°.

EXAMPLE 9

1.1 g of IIa, 2.87 g of 2,4-dimethoxybenzoic acid morpholide imidyl chloride, 6 ml of triethylamine and 5 ml of diethylene glycol dimethyl ether are heated at 120° for 30 minutes. After cooling down the mixture is worked up as customary to give 2-(2,4-dimethoxyphenyl)-1,3,4,7-tetraazaindene, m.p. 210°-215°.

EXAMPLE 10

11 g of IIa, 19 g of 2-methoxy-4-propargyloxybenzaldehyde (obtainable from 2,4-dihydroxybenzaldehyde via 2-hydroxy-4-propargyloxybenzaldehyde) and 10 g of sulfur are stirred at 180° for 10 hours in 200 ml of mesitylene, the mixture is evaporated to dryness, the residue is extracted with methanol, the solution is filtered and the filtrate is concentrated to 350 ml. The addition of ethereal hydrochloric acid precipitates 2-(2-methoxy-4-propargyloxyphenyl)-1,3,4,7-tetraazaindene hydrochloride; free base, m.p. 189°-190°.

EXAMPLE 11

11 g of IIb and 18.9 g of 2-methoxy-4-cyanomethoxybenzaldehyde are dissolved in 100 ml of dimethylacetamide, on addition of 19 g of sodium disulfite the solution is stirred at 140° for two hours and then worked up as customary to give 2-(4-cyanomethoxy-2-methoxyphenyl)-1,3,5,6-tetraazaindene, hydrochloride, m.p. 268°.

IIa or IIb combined with the appropriate aldehydes (such as, for example, p-propargyloxybenzaldehyde, m.p. 80°) give in a manner similar to that of Example 10 or 11 the other compounds given in Example 1.

EXAMPLE 12

24.1 g of 2-(4-hydroxy-2-methoxyphenyl)-1,3,5,6-tetraazaindene are dissolved in a calculated amount of 2N sodium hydroxide solution, the solution is evaporated to dryness, and residual water is removed by twice adding toluene and evaporating. The resulting Na salt is taken up in 300 ml of dimethylformamide, 8 ml of propargyl chloride are added, and the mixture is stirred at 20° for 16 hours. The mixture is worked up as customary using water and ethyl acetate, to give 2-(2-methoxy-4-propargyloxyphenyl)-1,3,5,6-tetraazaindene, m.p. 224°.

The corresponding hydroxy compounds give in a similar manner by etherification the other ethers given in Example 1.

EXAMPLE 13

A mixture of 10 g of 2-(4-acetoxy-2-methoxyphenyl)-1,3,4,7-tetraazaindene (obtainable by condensing IIa with 4-acetoxy-2-methoxybenzoic acid), 100 ml of methanol and 100 ml of a 2N aqueous NaOH solution is left to stand at 20° for 16 hours. The customary working up gives 2-(4-hydroxy-2-methoxyphenyl)-1,3,4,7-tetraazaindene.

On alkaline hydrolysis in a similar manner the corresponding acetoxy compounds give the other hydroxy compounds mentioned in Example 1.

EXAMPLE 14

A solution of 10 g of 2-(4-benzyloxy-2-methoxyphenyl)-1,3,5,6-tetraazaindene hydrochloride (obtainable by condensing IIb with 4-benzyloxy-2-methoxybenzoic acid) in 150 ml of methanol is hydrogenated at 20° over 5 g of 5% Pd-C under 1 bar until the end of hydrogen absorption, is filtered, and worked up as customary to give 2-(4-hydroxy-2-methoxyphenyl)-1,3,5,6-tetraazaindene.

On hydrogenolysis in a similar manner the corresponding benzyl ethers or benzyl thioethers give the other hydroxy or mercapto compounds mentioned in Example 1.

EXAMPLE 15

In a manner similar to that of Example 12, conversion of 2-(4-mercapto-2-methoxyphenyl)-1,3,5,6-tetraazaindene into the Na salt and subsequent reaction with ethyl iodide gives 2-(2-methoxy-4-ethylthiophenyl)-1,3,5,6-tetraazaindene, m.p. 248°.

On thioetherification in a similar manner the corresponding mercapto compounds give the other thioethers described in Example 1.

EXAMPLE 16

10 ml of 30% strength $H_2O_2$ are added to a boiling solution of 2.84 g of 2-(4-ethylthio-2-methoxyphenyl)-1,3,5,6-tetraazaindene in 50 ml of ethanol, and the mixture is then boiled for 3 hours. Cooling down and customary working up gives 2-(4-ethylsulfinyl-2-methoxyphenyl)-1,3,5,6-tetraazaindene.

Oxidation in a similar manner of the corresponding thioethers gives the other sulfinyl compounds described in Example 1.

The examples which follow relate to pharmaceutical preparations which contain compounds of the formula I or their acid addition salts.

EXAMPLE A: TABLETS

A mixture of 1 kg of 2-(2,4-dimethoxyphenyl)-1,3,5,6-tetraazaindene, 4 kg of lactose, 1.2 kg of potato starch, 0.2 kg of talc and 0.1 kg of magnesium stearate is conventionally compression-moulded into tablets in such a way that each tablet contains 100 mg of active compound.

EXAMPLE B: COATED TABLETS

Tablets are compression-moulded in a manner similar to that of Example A, and then coated in a customary manner with a coating of sucrose, potato starch, talc, tragacanth and colouring.

EXAMPLE C: CAPSULES 10 kg of 2-(2-methoxy-4-propargyloxyphenyl)-1,3,5,6-tetraazaindene are filled in a customary manner into hard gelatine capsules in such a way that each capsule contains 50 mg of active compound.

EXAMPLE D: AMPOULES

A solution of 1 kg of 2-(2,4-dimethoxyphenyl)-1,3,4,7-tetraazaindene fumarate in 100 liters of twice-distilled water is filtered under sterile conditions, the filtrate is filled into ampoules, which are lyophilised under sterile conditions and sealed under sterile conditions. Each ampoule contains 50 mg of active compound.

It is possible to obtain in a similar manner tablets, coated tablets, capsules and ampoules which contain one or more of the other active compounds of the formula I and/or their physiologically acceptable acid addition salts.

On investigation of the positive inotropic effect on an isolated guineapig atrium (method in line with Arzneimittelforschung, Loc. cit., page 162), some characteristic compounds of the formula I gave the following relative effectiveness values by comparison with Amrinon:

| Substance | | Effectiveness |
|---|---|---|
| Amrinon (comparative substance) | | 1 |
| Formula I, | | |
| A = | Ar = | |
| —CH=N—N=CH— | 2-Methoxy-4-propargyloxyphenyl | 70 |
| —N=CH—CH=N— | 2,4-Dimethoxyphenyl | 41 |
| —N=CH—CH=N— | 2-Methoxy-4-propargyloxyphenyl | 41 |
| —CH=N—N=CH— | 4-Cyanomethoxy-2-methoxyphenyl | 22 |
| —CH=N—N=CH— | 2,4-Dimethoxyphenyl | 20 |
| —N=CH—CH=N— | p-Propargyloxyphenyl | 12 |

Based on these results, a clinician can design an optimum dosage for any given patient by routine and standard experimentation.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A method of treating cardiac insufficiency, comprising administering a positive inotropic effective amount of a 2-aryltetraazaindene of the formula

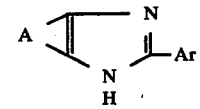

wherein —A— is —N=CH—CH=N— or —CH=N—N=CH—, Ar is unsubstituted phenyl or phenyl mono-, di- or tri-substituted by hydroxyl, mercapto, dialkylamino, trifluoromethyl and/or —Z—R groups, Z is —O—, —S— or —SO— and R is alkyl, alkenyl and alkynyl groups each having up to 5 C atoms, or a physiologically acceptable salt thereof.

2. A method according to claim 1, said compound being 2-(2,4-dimethoxyphenyl)-1,3,4,7-tetraazaindene.

3. A method according to claim 1, said compound being 2-(2-methoxy-4-propargyloxyphenyl)-1,3,4,7-tetraazaindene.

4. A method according to claim 1, said compound being 2-(4-cyanomethoxy-2-methoxyphenyl)-1,3,4,7-tetraazaindene.

5. A method according to claim 1, said compound being 2-(2,4-dimethoxyphenyl)-1,3,5,6-tetraazaindene.

6. A method according to claim 1, said compound being 2-(2-methoxy-4-propargyloxyphenyl)-1,3,4,7-tetraazaindene.

7. A method according to claim 1, said compound being 2-(4-cyanomethoxy-2-methoxyphenyl)-1,3,5,6-tetraazaindene.